(12) United States Patent
Liang et al.

(10) Patent No.: US 12,402,817 B2
(45) Date of Patent: Sep. 2, 2025

(54) BIOLOGICAL DETECTION APPARATUSES, SYSTEMS AND METHODS

(71) Applicants: Beijing BOE Technology Development Co., Ltd., Beijing (CN); BOE Technology Group Co., Ltd., Beijing (CN)

(72) Inventors: Kui Liang, Beijing (CN); Shuobin Liang, Beijing (CN)

(73) Assignees: Beijing BOE Technology Development Co., Ltd., Beijing (CN); BOE Technology Group Co., Ltd., Beijing (CN)

( * ) Notice: Subject to any disclaimer, the term of this patent is extended or adjusted under 35 U.S.C. 154(b) by 701 days.

(21) Appl. No.: 17/359,604

(22) Filed: Jun. 27, 2021

(65) Prior Publication Data

US 2022/0192547 A1 Jun. 23, 2022

(30) Foreign Application Priority Data

Dec. 23, 2020 (CN) .......................... 202011545958.0

(51) Int. Cl.
*A61B 5/145* (2006.01)
*A61B 5/00* (2006.01)
(Continued)

(52) U.S. Cl.
CPC ...... *A61B 5/14546* (2013.01); *A61B 5/02055* (2013.01); *A61B 5/024* (2013.01);
(Continued)

(58) Field of Classification Search
CPC . A61B 5/14546; A61B 5/02055; A61B 5/024; A61B 5/14517; A61B 5/1468;
(Continued)

(56) References Cited

U.S. PATENT DOCUMENTS 6,811,663 B1 11/2004 Freeman et al.
2016/0022187 A1* 1/2016 Pushpala ............ A61B 5/14503
600/347

(Continued)

FOREIGN PATENT DOCUMENTS

CN 101365381 A 2/2009
CN 106983507 A 7/2017

(Continued)

OTHER PUBLICATIONS

Huang et al., A Wireless Flexible Wearable Biopotential Acquisition System Utilizing Parylene Based Microneedle Array, 2019, 20th International Conference on Solid-State Sensors, Actuators and Microsystems & Eurosensors XXXIII [Transducers & Eurosensors XXXIII], Berlin, Germany, 2019, pp. 298-301 (Year: 2019).*

(Continued)

*Primary Examiner* — James Lin
*Assistant Examiner* — Sommer Yousef Osman
(74) *Attorney, Agent, or Firm* — IPro, PLLC

(57) ABSTRACT

Biological detection apparatuses, systems and methods are provided. A biological detection apparatus may include a flexible substrate and a biosensor. The biosensor is provided on the flexible substrate and configured to obtain substance information of a living body.

19 Claims, 9 Drawing Sheets

(51) Int. Cl.
  *A61B 5/0205* (2006.01)
  *A61B 5/024* (2006.01)
  *A61B 5/1468* (2006.01)

(52) U.S. Cl.
  CPC ........ *A61B 5/14517* (2013.01); *A61B 5/1468* (2013.01); *A61B 5/685* (2013.01); *A61B 2560/0214* (2013.01); *A61B 2562/0271* (2013.01); *A61B 2562/028* (2013.01); *A61B 2562/164* (2013.01)

(58) Field of Classification Search
  CPC ............ A61B 5/685; A61B 2560/0214; A61B 2562/0271; A61B 2562/028; A61B 2562/164; A61B 2503/10; A61B 2562/125; A61B 5/01; A61B 5/02438; A61B 5/1477; A61B 5/1486; A61B 5/02444; G01N 27/3272; G01N 27/3273; G01N 27/3333
  See application file for complete search history.

(56) References Cited

U.S. PATENT DOCUMENTS

| | | | |
|---|---|---|---|
| 2017/0128009 A1 | 5/2017 | Pushpala et al. | |
| 2019/0117083 A1 | 4/2019 | Wang et al. | |
| 2020/0087810 A1* | 3/2020 | Hosseini | G01N 27/30 |
| 2022/0080193 A1* | 3/2022 | Demiryurek | A61N 1/325 |

FOREIGN PATENT DOCUMENTS

| | | |
|---|---|---|
| CN | 108975266 A | 12/2018 |
| CN | 109549627 A | 4/2019 |
| CN | 109646015 A | 4/2019 |
| CN | 110073038 A | 7/2019 |
| CN | 110179457 A | 8/2019 |
| CN | 110974251 A | 4/2020 |

OTHER PUBLICATIONS

Beken Corporation, BK3231 Bluetooth HID SoC Datasheet, 2011, iq.direct/datasheets/BK3231.pdf, p. 1-12 (Year: 2011).*
Shin et al., Microfluidic platform for cell analysis using through-polydimethylsiloxane micro-tip electrode array, 2019, Microelectronic Engineering, 215, 1-7. (Year: 2019).*
Kim et al., Fabrication and Measurement of Microtip Electrode Array Integrated With Self-Aligned Hemispherical Cell Trapping PDMS Template, 2019 IEEE Sensors Journal, vol. 19, No. 20 (Year: 2019).*
Cheng et al., English translation of CN109646015A, 2019 (Year: 2019).*
Soltanzadeh, Development of Microneedle Array Electrodes for Transcutaneous Neural Stimulation and Recording Applications, 2019, University of Manitoba (Year: 2019).*
Xu, Gang, et al. "Battery free and wireless epidermal electrochemical system with all printed stretchable electrode array for multiplexed in situ sweat analysis." Advanced Materials Technologies 4.7 (2019): 1800658.
Flexible and Printed Wearable Electrochemical Sensor.
Latest Research Progress of Microneedle Processing Technology.
Wearable electrophysiological signal acquisition system based on CNT/aPDMS flexible dry electrode.
CN 2020115459580 first office action dated Dec. 25, 2024.

* cited by examiner

BIOLOGICAL DETECTION APPARATUSES, SYSTEMS AND METHODS

CROSS-REFERENCE TO RELATED APPLICATIONS

The present disclosure claims a priority of the Chinese patent application No. 202011545958.0 filed on Dec. 23, 2020 and entitled "BIOLOGICAL DETECTION APPARATUSES, SYSTEMS AND METHODS", which is incorporated herein by reference in its entirety.

TECHNICAL FIELD

The present disclosure relates to the field of sensor technology, in particular to a biological detection apparatus, a biological detection system, and a biological detection method.

BACKGROUND

An abnormal change in sweat composition during exercise of a human body is related to a blood viscosity of the human body or directly indicates health of the human body. For example, sodium ions, as the most abundant electrolytes in human sweat, are very important for sweat secretion. A concentration of the sodium ions may reflect various kinds of disorders of water-electrolyte metabolism in the human body. Therefore, a detection of substances such as the sodium ions and potassium ions in sweat during exercise has important health guidance significance for either athletes or ordinary people.

SUMMARY

The present disclosure provides a biological detection apparatus, a biological detection system, and a biological detection method.

According to an aspect of the present disclosure, there is provided a biological detection apparatus, including:
 a flexible substrate; and
 a biosensor provided on the flexible substrate and configured to obtain substance information of a living body.

Optionally, the biological detection apparatus may further include:
 a communication module, provided at a side of the flexible substrate and connected with the biosensor, and configured to send the substance information to a terminal device, and
 the biological detection apparatus may further include:
 an analog-to-digital converter, provided at the side of the flexible substrate and connected with the biosensor and the communication module, and configured to perform an analog-to-digital conversion on the substance information and send the converted substance information to the communication module.

Optionally, the biosensor is provided at a side of the flexible substrate facing the living body and located within a boundary of the flexible substrate.

Optionally, at least a part of the biosensor is located outside a boundary of the flexible substrate.

Optionally, the biological detection apparatus may further include at least one of:
 a temperature sensor, provided at a side of the flexible substrate facing the living body and configured to detect temperature information of the living body; or
 a heart rate sensor, provided at the side of the flexible substrate facing the living body and configured to detect heart rate information of the living body.

Optionally, the biological detection apparatus may further include:
 a power supply module, provided at a side of the flexible substrate facing away from the living body and connected with the biosensor to supply power to the biosensor.

Optionally, the biosensor may include a microelectrode structure, and the microelectrode structure may include:
 a first insulating layer; and
 an electrode layer provided at a side of the first insulating layer.

Optionally, the biosensor may include a microelectrode structure, and the microelectrode structure may include:
 a first insulating layer;
 a protrusion provided at a side of the first insulating layer; and
 an electrode layer conformally covering the first insulating layer and the protrusion.

Optionally, the microelectrode structure may further includes:
 a second insulating layer provided at a side of the electrode layer facing away from the first insulating layer, and provided with an opening through which the protrusion protrudes.

Optionally, an angle between a side surface and a bottom surface of the protrusion is an acute angle.

Optionally, the protrusion has a tapered shape.

Optionally, the protrusion has a maximum width of less than or equal to 10 µm in a direction parallel to the first insulating layer, and the protrusion is made of an insulating material.

Optionally, the protrusion and the first insulating layer are structurally integrated.

Optionally, the electrode layer includes one or more electrode regions separated from each other, and the first insulating layer is provided with a plurality of protrusions correspondingly to each of the electrode regions.

Optionally, the electrode layer includes a reference electrode region and one or more working electrode regions; or
 the electrode layer includes a reference electrode region, a counter electrode region and one or more working electrode regions.

Optionally, a distance between adjacent two of the electrode regions is 0.5 cm-2 cm.

Optionally, the microelectrode structure may further include:
 a first sensitive functional layer at least covering an area of the electrode layer corresponding to the protrusion;
 an auxiliary layer at least covering an area of the first sensitive functional layer corresponding to the protrusion, and provided with a first through-hole exposing the first sensitive functional layer, the first through-hole being provided in an area of the auxiliary layer corresponding to a top end of the protrusion, and a distance between the auxiliary layer and the electrode layer being less than or equal to 100 µm; and
 a second sensitive functional layer covering the auxiliary layer and filling the first through-hole so as to be in contact with the first sensitive functional layer.

Optionally, the first sensitive functional layer includes a sodium ion sensitive functional layer, a potassium ion sensitive functional layer, a calcium ion sensitive functional layer, a hydrogen ion sensitive functional layer or a chloride ion sensitive functional layer.

Optionally, the biosensor is configured to detect the substance information in sweat of the living body.

According to another aspect of the present disclosure, there is provided a biological detection system, including a biological detection apparatus, where the biological detection apparatus includes:

a flexible substrate; and a biosensor provided on the flexible substrate and configured to obtain substance information of a living body.

According to yet another aspect of the present disclosure, there is provided a biological detection method, including:

obtaining first substance information of a living body by using a biological detection apparatus; and replacing a biosensor of the biological detection apparatus to obtain second substance information of the living body, where, the biosensor is provided on a flexible substrate of the biological detection apparatus, and is configured to obtain the first substance information and/or the second substance information of the living body.

Optionally, the first substance information or the second substance information includes a sodium ion concentration, a potassium ion concentration, a calcium ion concentration, a hydrogen ion concentration, or a chloride ion concentration.

DETAILED DESCRIPTION OF THE EMBODIMENTS

Figure 1:
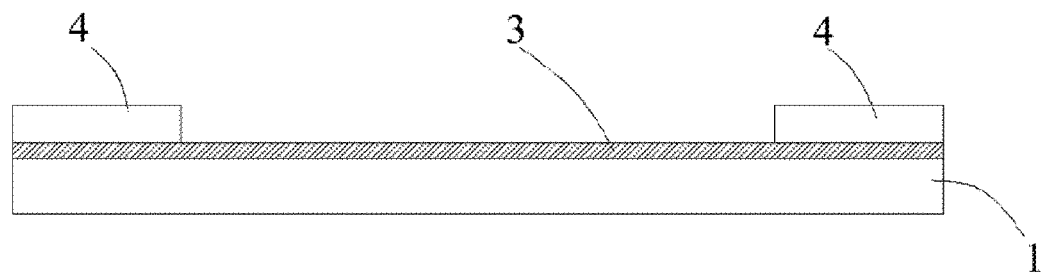
FIG. 1 is a schematic diagram of a microelectrode structure according to an embodiment of the present disclosure.

Exemplary embodiments will be described in detail herein, and examples thereof are illustrated in the drawings. When the following description refers to the drawings, the same numbers in different drawings indicate the same or similar elements, unless otherwise indicated. Implementations described in the following exemplary embodiments do not represent all implementations in accordance with the present disclosure. Rather, they are merely examples of apparatuses and methods in accordance with some aspects of the present disclosure as detailed in the appended claims.

Terms used in the present disclosure are merely for the purpose of describing particular embodiments, and are not intended to limit the present disclosure. Unless otherwise defined, technical terms or scientific terms used in the present disclosure shall have general meanings understood by those ordinary skilled in the art to which the present disclosure belongs. "First", "second" and other similar words used in the specification and claims of the present disclosure do not indicate any sequence, quantity or importance, but are only used to distinguish different components. Similarly, "one" or "a" and other similar words do not mean a quantity limitation, but mean at least one. "A plurality of" or "several" means two or more. Unless otherwise indicated, "front", "rear", "lower" and/or "upper" and other similar words are only for convenience of description, and are not limited to a position or a spatial orientation. "Include" or "comprise" and other similar words mean that elements or items before "include" or "comprise" cover elements or items listed after "include" or "comprise" and their equivalents, and do not exclude other elements or items. "Connect" or "couple" and other similar words are not limited to physical or mechanical connections, and may include electrical connections, whether direct or indirect. Terms determined by "a", "the" and "said" in their singular forms in the specification of the present disclosure and the appended claims are also intended to include plural forms, unless clearly indicated otherwise in the context. It should also be understood that the term "and/or" as used herein refers to and includes any or all possible combinations of one or more of associated listed items.

A detection of substances such as sodium ions and potassium ions in sweat during exercise of a human body has important health guidance significance for either athletes or ordinary people. However, information on the substances such as the sodium ions and the potassium ions cannot be detected in the related art.

Embodiments of the present disclosure provide a biological detection apparatus. The biological detection apparatus may be a wearable biological detection apparatus, or an attachable biological detection apparatus such as a patch. The biological detection apparatus may include a flexible substrate and a biosensor. The biosensor is provided on the flexible substrate and configured to obtain substance information of a living body. Further, the biosensor may be configured to detect the substance information in sweat of the living body. The biosensor and the flexible substrate are two independent components, and the biosensor is not a part of the flexible substrate.

During use of the biological detection apparatus according to the embodiments of the present disclosure, the flexible substrate is attached to the skin surface of the living body to be detected, and the biosensor is directed toward the living body to be detected, such that the substance information of the living body may be detected through the biosensor.

The biosensor may include a microelectrode structure. In an embodiment of the present disclosure, as shown in FIG. 1, the microelectrode structure may include a first insulating layer 1 and an electrode layer 3. The electrode layer 3 may be provided at a side of the first insulating layer 1. The first insulating layer 1 may be provided at a side of the flexible substrate facing the living body, and the electrode layer 3 may be provided at a side of the first insulating layer 1 facing away from the flexible substrate. The microelectrode structure may include a second insulating layer 4. The electrode layer 3 may be located between the first insulating layer 1 and the second insulating layer 4. The second insulating layer 4 may be provided with a window exposing the electrode layer 3.

Figure 2:
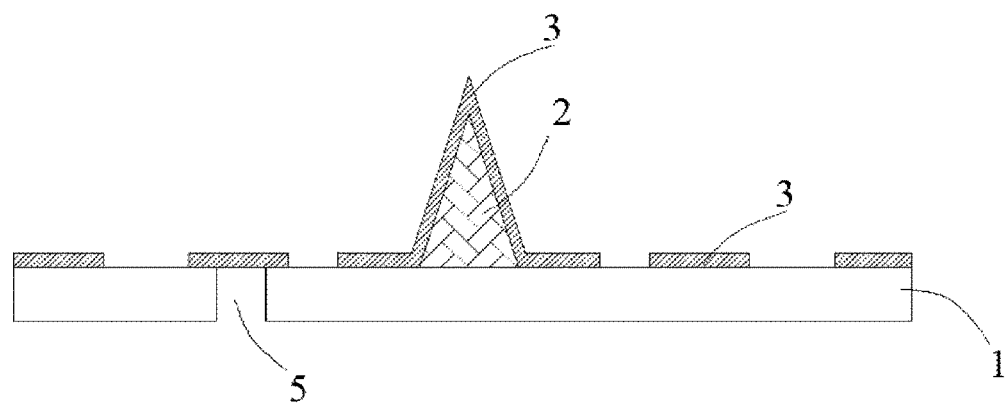
FIG. 2 is a schematic diagram of a microelectrode structure with a protrusion according to an embodiment of the present disclosure.

In another embodiment of the present disclosure, as shown in FIG. 2, the microelectrode structure may include a first insulating layer 1, a protrusion 2 and an electrode layer 3.

The protrusion 2 is provided at a side of the first insulating layer 1. The electrode layer 3 conformally covers the first insulating layer 1 and the protrusion 2.

According to the microelectrode structure in the embodiment of the present disclosure, the protrusion 2 is provided on the first insulating layer 1, and the electrode layer 3 conformally covers the first insulating layer 1 and the protrusion 2, such that an area of the electrode layer 3 corresponding to the protrusion 2 also protrudes outward. In this way, an area of the electrode layer 3 provided on the first insulating layer 1 may be increased, and thus a contact area between the electrode layer 3 and the detected living body may be increased, thereby improving the detection accuracy.

Hereinafter, components of the microelectrode structure in the embodiment of the present disclosure will be described in detail.

Figure 13:
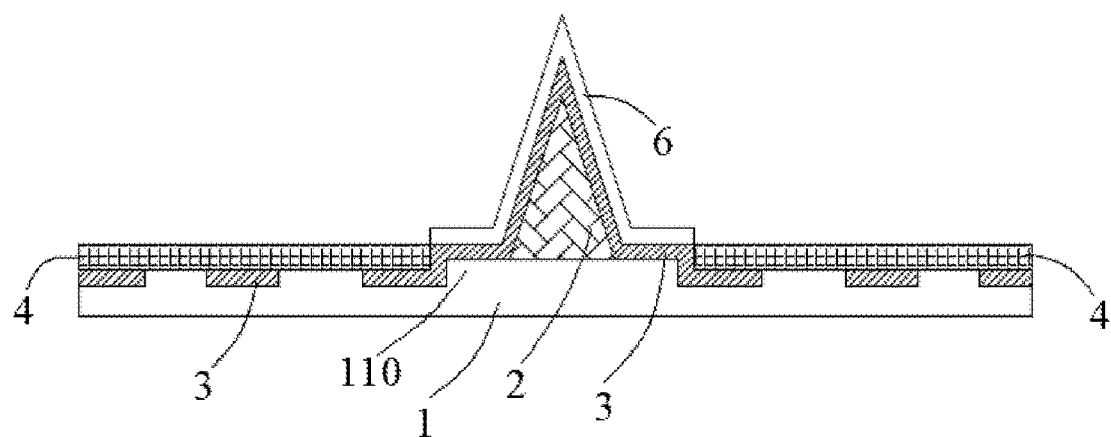
FIG. 13 is a schematic diagram after a first sensitive functional layer is formed in a method of preparing a microelectrode structure according to an embodiment of the present disclosure.

As shown in FIG. 2, the first insulating layer 1 may be made of an organic material such as a polymer material, such that the microelectrode structure has good flexibility, thereby ensuring good contact between the microelectrode structure and tissues of the living body while reducing damage to the tissues. The polymer material may include polyimide, parylene, polydimethylsiloxane, or the like. In other embodiments of the present disclosure, the first insulating layer 1 may be made of an inorganic material such as a silicon-based material, such that the microelectrode structure may have better biocompatibility and may be manufactured using a process compatible with a microelectronic process of CMOS. The first insulating layer 1 may include a first surface and a second surface opposite to each other. In addition, as shown in FIG. 13, a boss 110 may be formed on a side of the first insulating layer 1. The boss 110 may be a part of the first insulating layer 1.

As shown in FIG. 2, the protrusion 2 may be provided on the first insulating layer 1. The protrusion 2 may be provided on the first surface of the first insulating layer 1. The protrusion 2 may include a bottom surface and a side surface connected with each other. The bottom surface of the protrusion 2 faces the first surface of the first insulating layer 1 and mates with the first surface of the first insulating layer 1. An angle between the side surface and the bottom surface of the protrusion 2 may be an acute angle, that is, a cross section of the protrusion 2 may be gradually decreased in a direction away from the first insulating layer 1. Further, the protrusion 2 may have a tapered shape, such as a conical shape. In other embodiments of the present disclosure, the protrusion 2 may have a cylindrical shape, a prismatic shape, a truncated cone shape, or the like. The protrusion 2 may have the maximum width of less than or equal to 10 μm in a direction parallel to the first insulating layer 1. Taking the protrusion 2 being a cone as an example, a diameter of a bottom surface of the cone may be less than or equal to 10 μm. Since the maximum width of the protrusion 2 in the direction parallel to the first insulating layer 1 is relatively small, a larger number of protrusions 2 may be formed in a unit area of the first insulating layer 1. In other embodiments of the present disclosure, the maximum width of the protrusion 2 in the direction parallel to the first insulating layer 1 may be greater than 10 μm and less than 100 μm. A height of the protrusion 2 may be less than or equal to 10 μm. However, the height of the protrusion 2 may be greater than 10 μm. The protrusion 2 may be made of an insulating material, such as an inorganic insulating material, an organic insulating material, or the like. The organic insulating material may include polyimide, parylene, polydimethylsiloxane, or the like. The material of the protrusion 2 may be the same as the material of the first insulating layer 1. Further, the protrusion 2 and the first insulating layer 1 may be structurally integrated, that is, the protrusion 2 and the first insulating layer 1 may be integrally formed. In addition, the microelectrode structure may include a plurality of protrusions 2 arranged at intervals. In addition, as shown in FIG. 13, the protrusion 2 may be provided on the boss 110. The protrusion 2 may be located within a boundary of the boss 110, that is, the protrusion 2 has a lateral dimension smaller than that of the boss 110.

As shown in FIG. 2, the electrode layer 3 conformally covers the first insulating layer 1 and the protrusion 2, that is, an area of the electrode layer 3 corresponding to the protrusion 2 protrudes away from the protrusion 2. The electrode layer 3 may conformally cover the first insulating layer 1 and the protrusion 2 by controlling a thickness of the electrode layer 3. Since the angle between the side surface and the bottom surface of the protrusion 2 is an acute angle, the electrode layer 3 covering the protrusion 2 is less prone to fracture. The electrode layer 3 may be made of a metal material, such as Au, Ag, Pd, and Pt. In addition, the first insulating layer 1 may be further provided with a second through-hole 5 exposing the electrode layer 3, such that an external circuit may be electrically connected with the electrode layer 3 through the second through-hole 5.

Figure 3:
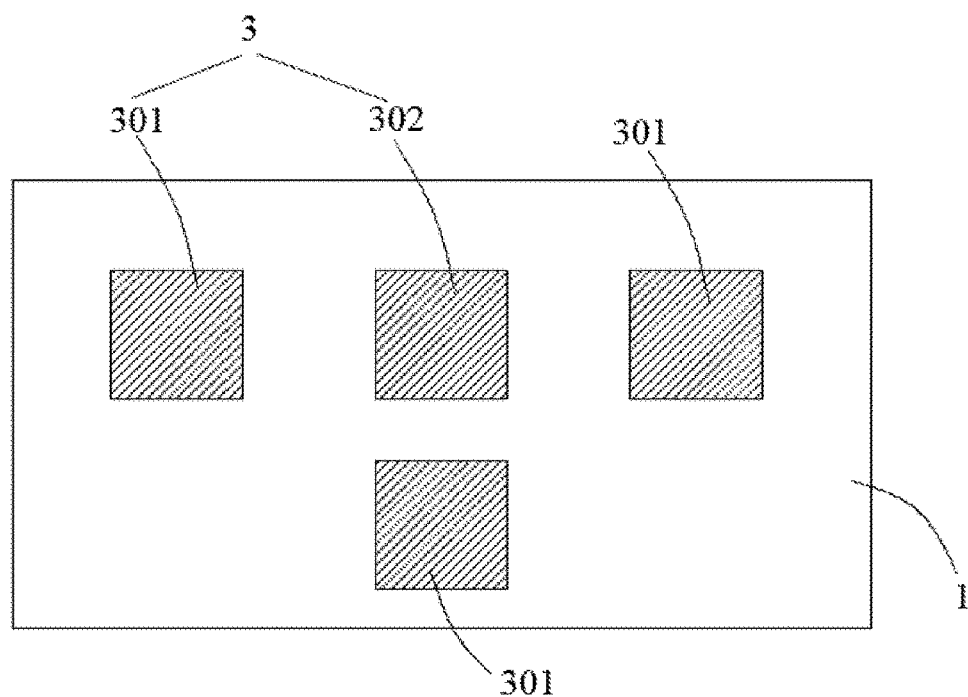
FIG. 3 is a schematic plan view of a microelectrode structure according to an embodiment of the present disclosure.

As shown in FIG. 3, the electrode layer 3 may include one or more electrode regions. Taking the electrode layer 3 including a plurality of electrode regions as an example, the plurality of electrode regions may be separated from each other. A distance between two adjacent electrode regions may be 0.5 cm-2 cm, for example, 0.5 cm, 0.8 cm, 1.3 cm, 1.5 cm, 2 cm, etc. In an embodiment of the present disclosure, the electrode layer 3 is a two-electrode system, that is, the plurality of electrode regions may include a reference electrode region 302 and one or more working electrode regions 301. In another embodiment of the present disclosure, the electrode layer 3 is a three-electrode system, that is, the plurality of electrode regions may include a reference electrode region 302, a counter electrode region, and one or more working electrode regions 301. The first insulating layer 1 may be provided with a plurality of protrusions 2 correspondingly to each of the electrode regions.

Figure 4:
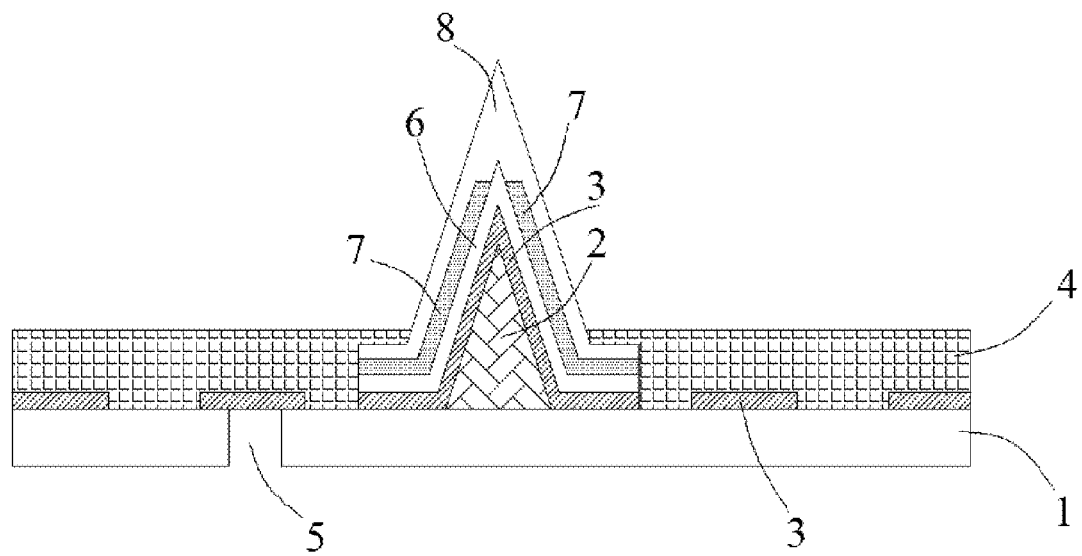
FIG. 4 is another schematic diagram of a microelectrode structure according to an embodiment of the present disclosure.

As shown in FIG. 4, the microelectrode structure according to the embodiment of the present disclosure may further include a second insulating layer 4. The second insulating layer 4 may be provided at a side of the electrode layer 3 facing away from the first insulating layer 1. The second insulating layer 4 may be provided with an opening through which the protrusion 2 protrudes, such that the protrusion 2 may be in close contact with the tissues of the living body, thereby improving the detection efficiency and accuracy. Taking the microelectrode structure including a plurality of protrusions 2 as an example, the microelectrode structure may include a plurality of openings, and the plurality of protrusions 2 may protrude through the plurality of openings in one-to-one correspondence. In other embodiments of the present disclosure, each of the electrode regions may correspond to one opening, that is, a plurality of protrusions 2 corresponding to each electrode region may be exposed through one opening. The second insulating layer 4 may be made of an organic material, such as a polymer material. The polymer material may include polyimide, parylene, polydimethylsiloxane, or the like. In other embodiments of the present disclosure, the second insulating layer 4 may be made of an inorganic material, such as a silicon-based material. The material of the second insulating layer 4 may be the same as the material of the first insulating layer 1. However, the material of the second insulating layer 4 may be different from the material of the first insulating layer 1.

Figure 5:
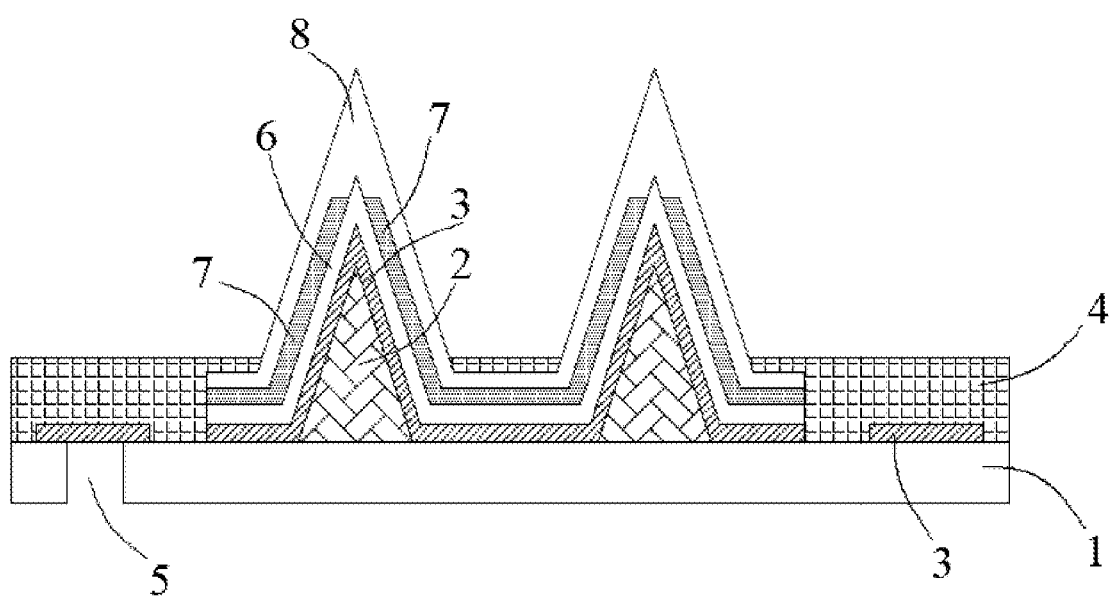
FIG. 5 is yet another schematic diagram of a microelectrode structure according to an embodiment of the present disclosure.

As shown in FIG. 4, the microelectrode structure according to the embodiment of the present disclosure may further include a first sensitive functional layer 6. In an embodiment of the present disclosure, the first sensitive functional layer 6 may include an ionophore or the like, such that the electrode layer 3 forms an ion selective electrode, enabling the microelectrode structure to be used to measure ions. For example, the first sensitive functional layer 6 may include a sodium ion sensitive functional layer, a potassium ion sensitive functional layer, a calcium ion sensitive functional layer, a hydrogen ion sensitive functional layer or a chloride ion sensitive functional layer, such that the microelectrode structure may be configured to measure sodium ion, potassium ion, calcium ion, hydrogen ion or chloride ion. In another embodiment of the present disclosure, the first sensitive functional layer 6 may include an enzyme such as glucose enzyme, such that the microelectrode structure may be configured to analyze glucose. The first sensitive functional layer 6 may also be configured to analyze lactic acid and the like. The first sensitive functional layer 6 at least covers an area of the electrode layer 3 corresponding to the protrusion 2. Further, taking the microelectrode structure including the second insulating layer 4 as an example, the first sensitive functional layer 6 at least covers an area of the electrode layer 3 corresponding to a portion of the protrusion 2 protruding through the opening. The microelectrode structure according to the embodiment of the present disclosure may further include an auxiliary layer 7. The auxiliary layer 7 at least covers an area of the first sensitive functional layer 6 corresponding to the protrusion 2. The auxiliary layer 7 may be provided with a first through-hole exposing the first sensitive functional layer 6. The first through-hole is located outside the opening, that is, a portion of the first sensitive functional layer 6 located outside the opening is exposed through the first through-hole. A distance between the auxiliary layer 7 and the electrode layer 3 may be less than or equal to 100 μm, such that a capillary channel may be formed between the auxiliary layer 7 and the electrode layer 3 to generate a capillary force, thereby further improving the extraction and adsorption capacity of the microelectrode structure for liquids such as tissue fluids and sweat of the living body. Further, the distance between the auxiliary layer 7 and the electrode layer 3 may be less than or equal to 10 μm, for example, 10 μm, 9 μm, 7 μm, 6 μm, 5 μm, etc. In addition, taking the protrusion 2 having a tapered shape as an example, the first through-hole may be provided in an area of the auxiliary layer 7 corresponding to a top end of the protrusion 2. The auxiliary layer 7 may be made of an inorganic material, such as a metal material. However, the auxiliary layer 7 may be made of an organic material. The material of the auxiliary layer 7 may be the same as the material of the electrode layer 3. The microelectrode structure according to the embodiment of the present disclosure may further include a second sensitive functional layer 8. The second sensitive functional layer 8 may cover the auxiliary layer 7 and fill the first through-hole so as to be in contact with the first sensitive functional layer 6. The extraction and adsorption capacity of the microelectrode structure for liquids may be further improved with the second sensitive functional layer 8. The second sensitive functional layer 8 has the same composition as the first sensitive functional layer 6. In addition, when there are a plurality of protrusions 2 on the first insulating layer 1, the resulting microelectrode structure is as shown in FIG. 5.

As shown in FIGS. 3 and 4, taking the electrode layer 3 including the working electrode regions 301 and the reference electrode region 302 as an example, the first sensitive functional layer 6 may cover the working electrode regions 301. A conductive organic layer may be further provided between the working electrode regions 301 and the first sensitive functional layer 6. The conductive organic layer may be made of PEDOT (poly(3,4-ethylenedioxythiophene)):PSS (poly(styrenesulfonate)), PEDOT (poly(3,4-ethylenedioxythiophene)):PEGDA (poly(ethylene glycol) diacrylate), etc. PEDOT:PSS is a blend of PEDOT and PSS. PEDOT:PEGDA is a blend of PEDOT and PEGDA. Taking the conductive organic layer made of PEDOT:PSS as an example, a process of preparing the conductive organic layer may include: preparing a solution containing 0.01 mol/L EDOT and 0.1 mol/L NaPSS, and depositing it on the working electrode region 301 by constant-current electrochemical polymerization of an external Ag/AgCl electrode, where a constant current of 2 mA·cm$^{-2}$ may be applied to generate polymerization charges on each working electrode region 301.

When measuring sodium ions, the first sensitive functional layer 6 may include a sodium ion selective film. A process of preparing the sodium ion selective film may include: preparing a mixture containing sodium ionophore X (1% w/w (weight by weight)), Na-TFPB (Sodium tetrakis [3,5-bis(trifluoromethyl)phenyl]borate) (0.55% w/w), PVC (polyvinyl chloride) (33% w/w) and DOS (dioctyl sebacate) (65.45% w/w), and dissolving 100 mg of the mixture in 660 μL THF (Tetrahydrofuran) to form ion selective solution; and forming the first sensitive functional layer 6 by a liquid-phase deposition method using the formed ion selective solution as a raw material, where the sodium ionophore X may be 4-tert-butylcalix[4]arene-tetraacetic acid tetraethyl ester. The microelectrode structure according to the present disclosure has high ion concentration detection sensitivity, which may reach 70-80 mv/dec when taking sodium ions as an example.

When measuring potassium ions, the first sensitive functional layer 6 may include a potassium ion selective film. A process of preparing the potassium ion selective film may include: preparing a mixture containing valinomycin (2% w/w), Na-TFPB (0.5% w/w), PVC (32.8% w/w) and DOS (64.7% w/w), and dissolving 100 mg of the mixture in 350 μL cyclohexanone to form ion selective solution; and forming the first sensitive functional layer 6 by a liquid-phase deposition method using the formed ion selective solution as a raw material.

When measuring chloride ions, the first sensitive functional layer 6 may include a chloride ion selective film. A process of preparing the chloride ion selective film may include: using a micropipette to place 0.1 mol/L FeCl$_3$ solution on the top of the evaporated Ag electrode for 1 minute to form Ag/AgCl.

When measuring calcium ions, the first sensitive functional layer 6 may include a calcium ion selective film. A process of preparing the calcium ion selective film may include: preparing a mixture containing ETH129 (Calcium Ionophore II) (1% w/w), Na-TFPB (0.5% w/w), PVC (33% w/w) and DOS (65.5% w/w), and dissolving 100 mg of the mixture in 660 μL THF to form ion selective solution; and forming the first sensitive functional layer 6 by a liquid-phase deposition method using the formed ion selective solution as a raw material.

When measuring hydrogen ions, the first sensitive functional layer 6 may include a hydrogen ion selective film. A process of preparing the hydrogen ion selective film may include: distilling aniline at a vapor temperature of 100° C. and a pressure of 13 mmHg; forming PANI (polyaniline) in 0.1 mol/L aniline/0.1 mol/L HCl solution; and performing 25 cycles of PANI deposition from −0.2V to 1V at 200 mV/s using cyclic voltammetry to form the first sensitive functional layer 6.

When measuring ions, the reference electrode region 302 may also be covered with a functional layer. A process of preparing the functional layer may include: dissolving 79.1 mg PVB (polyvinyl butyral) and 50 mg NaCl in 1 mL Methanol to prepare a film mixture solution, adding 2 mg F127 and 0.2 mg Multiwall carbon nanotubes to the film mixture solution, and forming the functional layer on the reference electrode region 302 by a liquid-phase deposition method.

Figure 6:
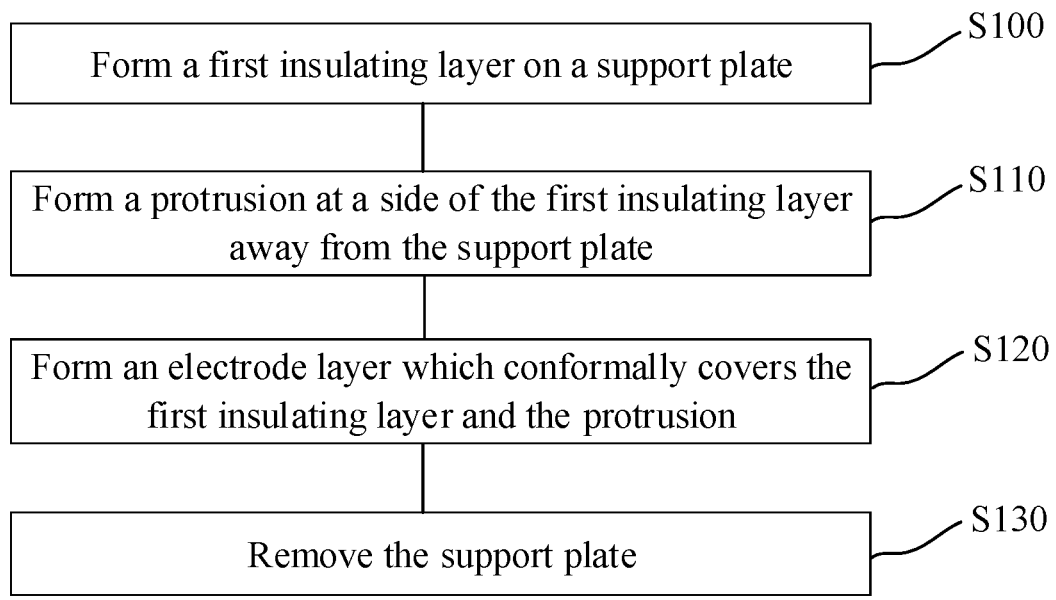
FIG. 6 is a flowchart of a method of preparing a microelectrode structure according to an embodiment of the present disclosure.

The embodiments of the present disclosure also provide a method of manufacturing the microelectrode structure, which is configured to manufacture the above microelectrode structure. As shown in FIG. 6, the method of manufacturing the microelectrode structure may include steps S100-S130.

At step S100, a first insulating layer is formed on a support plate.

At step S110, a protrusion is formed at a side of the first insulating layer away from the support plate.

At step S120, an electrode layer is formed, and the electrode layer conformally covers the first insulating layer and the protrusion.

At step S130, the support plate is removed.

The microelectrode structure manufactured by the method according to the embodiment of the present disclosure and the microelectrode structure according to the above embodiments are the same, and thus have the same beneficial effects, which will not be repeated herein.

Hereinafter, steps in the method of manufacturing the microelectrode structure according to the embodiment of the present disclosure will be described in detail.

At step S100, a first insulating layer 1 is formed on a support plate 9.

Figure 7:
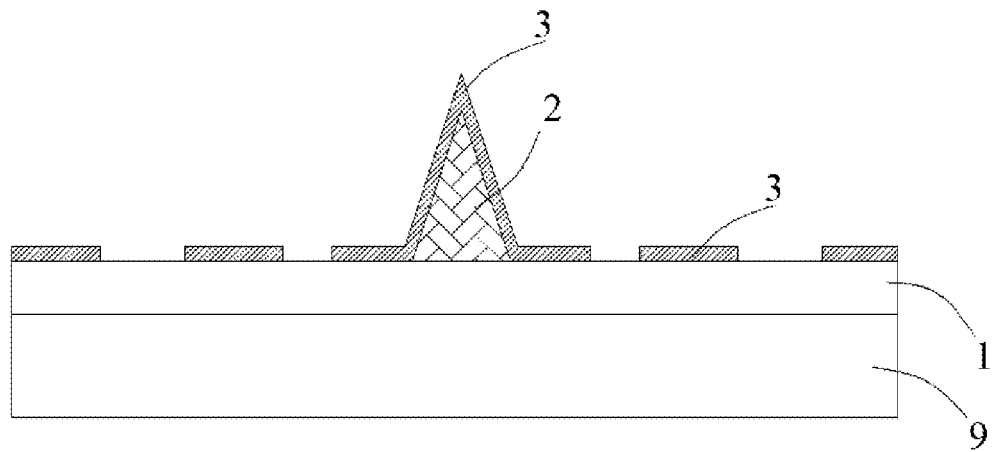
FIG. 7 is a schematic diagram after an electrode layer is formed in a method of preparing a microelectrode structure according to an embodiment of the present disclosure.

As shown in FIG. 7, the support plate 9 may be made of inorganic oxide, plastic material, or the like. The first insulating layer 1 may be prepared by a liquid-phase deposition process, such as a spin coating process, which is not particularly limited in the present disclosure.

At step S110, a protrusion 2 is formed at a side of the first insulating layer 1 away from the support plate 9.

As shown in FIG. 7, the protrusion 2 may be formed at the side of the first insulating layer 1 away from the support plate 9 through an imprint process or a transfer process. Since the protrusion 2 is prepared by an imprint process or a transfer process, the protrusion 2 with a larger size may be prepared. For example, a height of the protrusion 2 may be between 10 μm and 100 μm.

At step S120, an electrode layer 3 is formed, and the electrode layer 3 conformally covers the first insulating layer 1 and the protrusion 2.

As shown in FIG. 7, taking the electrode layer 3 made of a metal material including a plurality of electrode regions separated from each other as an example, forming the electrode layer 3 may include: forming an electrode material layer, which conformally covers the first insulating layer 1 and the protrusion 2; and patterning the electrode material layer to form the electrode layer 3. The electrode material layer may be prepared by an evaporation process. The electrode material layer may be patterned by a photolithography process to form the electrode layer 3 including a plurality of electrode regions. Taking the electrode layer 3 made of a conductive polymer as an example, the electrode layer 3 including a plurality of electrode regions may be formed by an inkjet printing process, which is not particularly limited in the present disclosure.

At step S130, the support plate 9 is removed.

Figure 8:
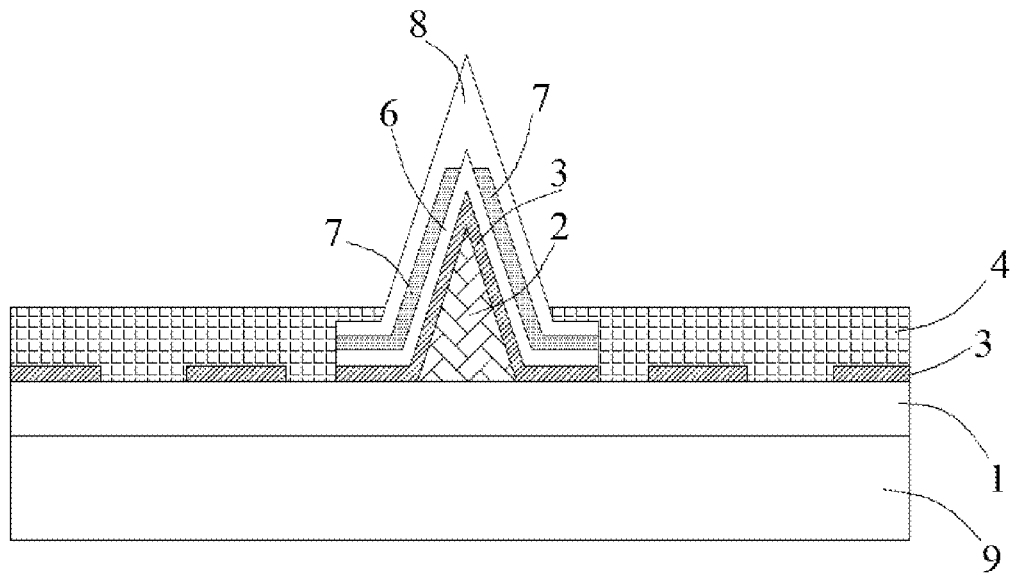
FIG. 8 is a schematic diagram after a second sensitive functional layer is formed in a method of preparing a microelectrode structure according to an embodiment of the present disclosure.

The support plate 9 may be removed by a chemical etching and peeling process, which is not particularly limited in the present disclosure. As shown in FIG. 8, before removing the support plate 9, the method of manufacturing the microelectrode structure according to the present disclosure may further include: forming a second insulating layer 4 at a side of the electrode layer 3 facing away from the first insulating layer 1. The second insulating layer 4 is provided with an opening through which the protrusion 2 protrudes. For example, forming the second insulating layer 4 may include: forming an insulating material layer at the side of the electrode layer 3 facing away from the first insulating layer 1; and patterning the insulating material layer to form the second insulating layer 4, where the second insulating layer 4 is provided with an opening through which the protrusion 2 protrudes. The insulating material layer may be prepared by a liquid-phase deposition process, such as a spin coating process, which is not particularly limited in the present disclosure. The insulating material layer may be patterned by a photolithography process in the present disclosure.

As shown in FIG. 8, before removing the support plate 9, the method of manufacturing the microelectrode structure according to the present disclosure may further include: forming a first sensitive functional layer 6, which at least covers an area of the electrode layer 3 corresponding to the protrusion 2. The first sensitive functional layer 6 may be prepared by a spin coating process. After forming the first sensitive functional layer 6, the method of manufacturing the microelectrode structure according to the present disclosure may further include: forming an auxiliary layer 7, which at least covers an area of the first sensitive functional layer 6 corresponding to the protrusion 2 and is provided with a first through-hole exposing the first sensitive functional layer 6, and a distance between the auxiliary layer 7 and the electrode layer 3 may be less than or equal to 100 μm. Taking the auxiliary layer 7 made of a metal material as an example, the auxiliary layer 7 may be prepared by an evaporation process. After forming the auxiliary layer 7, the method of manufacturing the microelectrode structure according to the present disclosure may further include: forming a second sensitive functional layer 8, which covers the auxiliary layer 7 and fills the first through-hole so as to be in contact with the first sensitive functional layer 6. The second sensitive functional layer 8 may be prepared by a spin coating process. In addition, the first through-hole of the auxiliary layer 7 is located outside the opening of the second insulating layer 4.

The method of manufacturing the microelectrode structure and the microelectrode structure according to the embodiments of the present disclosure belong to the same inventive concept, and descriptions of related details and beneficial effects may be referred to each other and will not be repeated.

Figure 9:
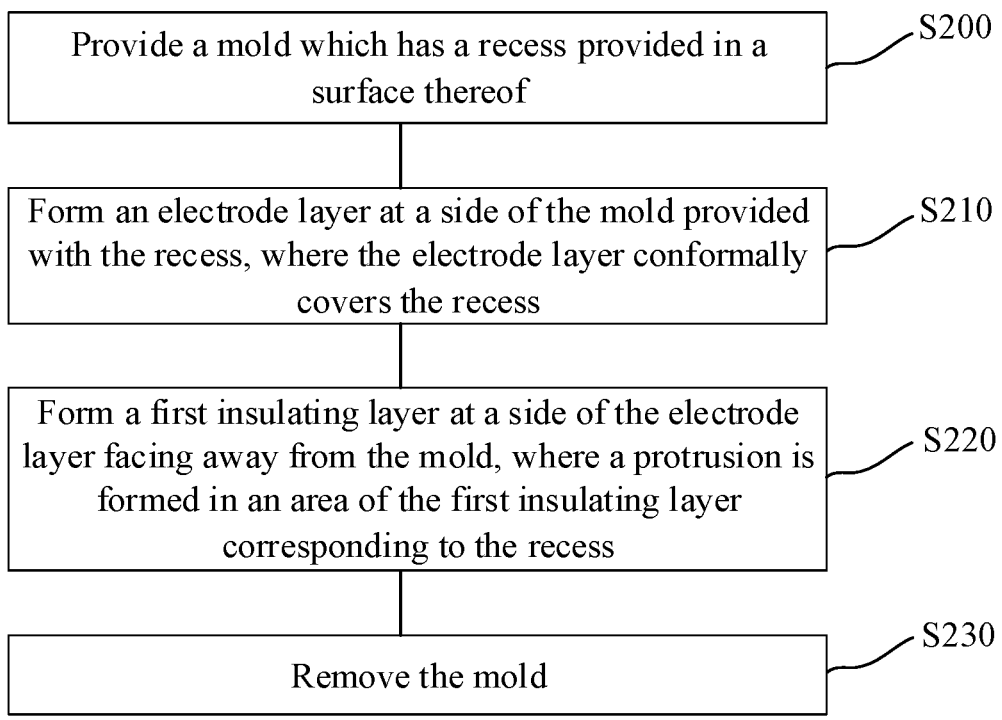
FIG. 9 is a flowchart of a method of preparing a microelectrode structure according to another embodiment of the present disclosure.

The embodiments of the present disclosure also provide a method of manufacturing the microelectrode structure, which is configured to manufacture the above microelectrode structure. As shown in FIG. 9, the method of manufacturing the microelectrode structure may include steps S200-S230.

At step S200, a mold is provided, and the mold has a recess provided in a surface thereof.

At step S210, an electrode layer is formed at a side of the mold provided with the recess, and the electrode layer conformally covers the recess.

At step S220, a first insulating layer is formed at a side of the electrode layer facing away from the mold, and a protrusion is formed in an area of the first insulating layer corresponding to the recess.

At step S230, the mold is removed.

The microelectrode structure manufactured by the method according to the embodiment of the present disclosure and the microelectrode structure according to the above embodiments are the same, and thus have the same beneficial effects, which will not be repeated herein.

Hereinafter, steps in the method of manufacturing the microelectrode structure according to the embodiment of the present disclosure will be described in detail.

At step S200, a mold 10 is provided, and the mold 10 has a recess 101 provided in a surface thereof.

Figure 10:
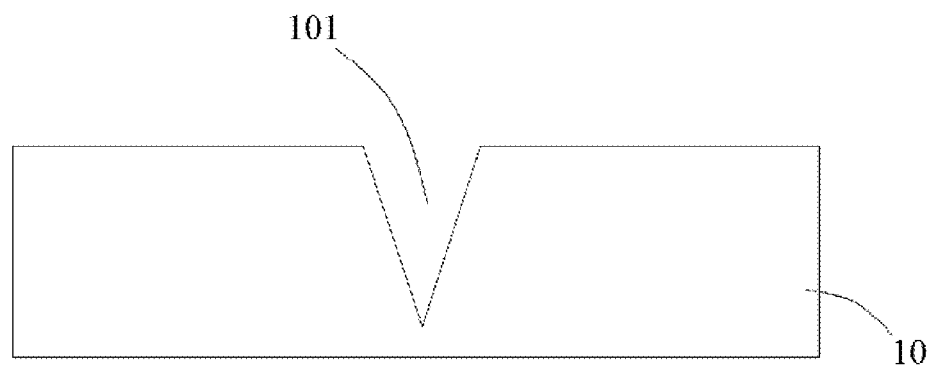
FIG. 10 is a schematic diagram of a mold in a method of preparing a microelectrode structure according to an embodiment of the present disclosure.

As shown in FIG. 10, the mold 10 may be made of silica gel or the like. An angle between a side surface of the recess 101 and the surface of the mold 10 may be an obtuse angle, that is, the recess 101 may have a flared structure. Further, the recess 101 may have a tapered structure, such as a cone.

At step S210, an electrode layer 3 is formed at a side of the mold 10 provided with the recess 101, and the electrode layer 3 conformally covers the recess 101.

Figure 11:
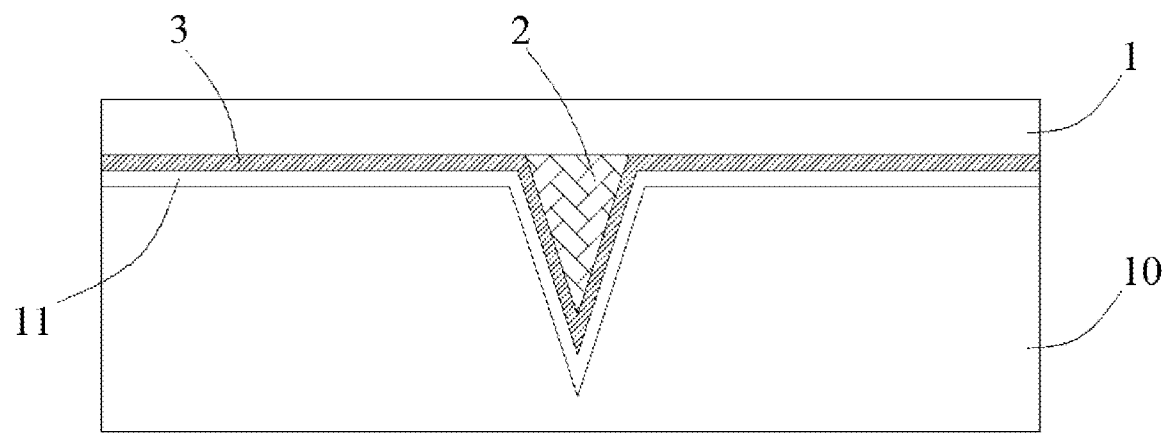
FIG. 11 is a schematic diagram after a first insulating layer is formed in a method of preparing a microelectrode structure according to an embodiment of the present disclosure.

For example, as shown in FIG. 11, forming the electrode layer 3 may include: forming a sacrificial layer 11 at the side of the mold 10 provided with the recess 101, and the sacrificial layer 11 conformally covers the recess 101; and forming the electrode layer 3 at a side of the sacrificial layer 11 facing away from the mold 10, and the electrode layer 3 conformally covers an area of the sacrificial layer 11 located in the recess 101. The sacrificial layer 11 may be made of aluminum, which is not particularly limited in the embodiment of the present disclosure. The sacrificial layer 11 conformally covers the recess 101, that is, an area of the sacrificial layer 11 corresponding to the recess 101 protrudes toward the recess 101. The electrode layer 3 may be prepared by an evaporation process or an inkjet printing process.

Figure 12:
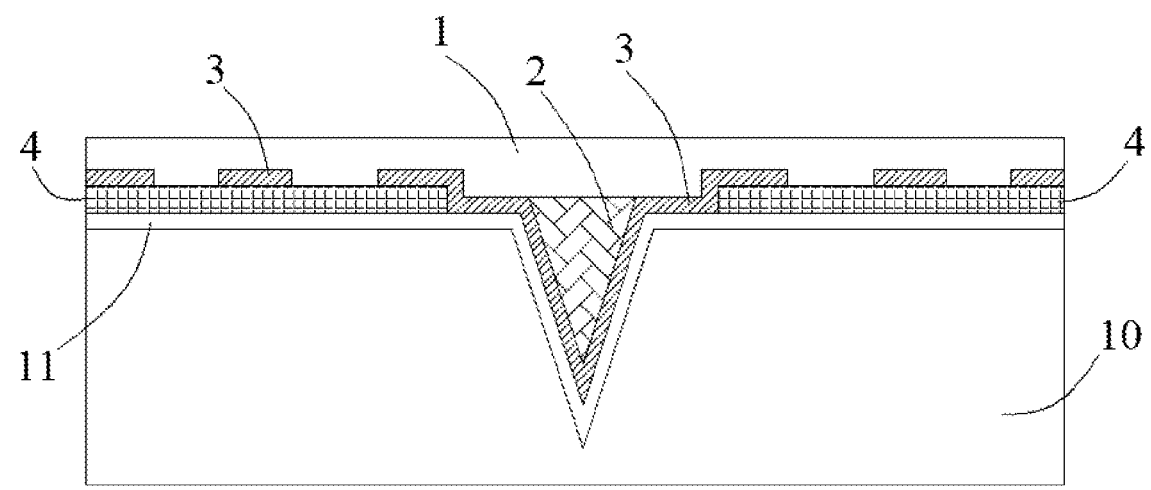
FIG. 12 is another schematic diagram after a first insulating layer is formed in a method of preparing a microelectrode structure according to an embodiment of the present disclosure.

In another embodiment of the present disclosure, as shown in FIG. 12, forming the electrode layer 3 at the side of the mold 10 provided with the recess 101 may include: forming a second insulating layer 4 at the side of the mold 10 provided with the recess 101, where the second insulating layer 4 has an opening through which the recess 101 is exposed; and forming the electrode layer 3 covering the second insulating layer 4 and the recess 101. The second insulating layer 4 may be prepared by a spin coating process. However, the second insulating layer 4 may also be formed at the side of the sacrificial layer 11 facing away from the mold 10.

At step S220, a first insulating layer 1 is formed at a side of the electrode layer 3 facing away from the mold 10, and a protrusion 2 is formed in an area of the first insulating layer 1 corresponding to the recess 101.

As shown in FIG. 11 and FIG. 12, the protrusion 2 is formed in the area of the first insulating layer 1 corresponding to the recess 101, that is to say, the first insulating layer 1 is non-conformally formed at the side of the electrode layer 3 facing away from the mold 10. The first insulating layer 1 may be prepared by a spin coating process. A height of the protrusion 2 may be less than or equal to 10 μm.

At step S230, the mold 10 is removed.

Taking the sacrificial layer 11 being formed between the electrode layer 3 and the mold 10 as an example, removing the mold 10 may include: removing the sacrificial layer 11 and the mold 10. For example, the sacrificial layer 11 may be removed through etching solution. An etching rate of the sacrificial layer 11 by the etching solution is greater than an etching rate of the electrode layer 3 by the etching solution. Taking the electrode layer 3 made of Au and the sacrificial layer 11 made of Al as an example, the etching solution may include acid etching solution.

As shown in FIGS. 11 and 4, if the second insulating layer 4 is not formed at the step S210, then after removing the mold 10, the method of manufacturing the microelectrode structure according to the embodiment of the present disclosure may further include: forming a second insulating layer 4 at a side of the electrode layer 3 facing away from the first insulating layer 1, where the second insulating layer 4 is provided with an opening through which the protrusion 2 protrudes.

In addition, as shown in FIG. 4, the method of manufacturing the microelectrode structure according to the present disclosure may further include: forming a first sensitive functional layer 6, which at least covers an area of the electrode layer 3 corresponding to the protrusion 2. The first sensitive functional layer 6 may be prepared by a spin coating process. After forming the first sensitive functional layer 6, the method of manufacturing the microelectrode structure according to the present disclosure may further include: forming an auxiliary layer 7, which at least covers an area of the first sensitive functional layer 6 corresponding to the protrusion 2 and is provided with a first through-hole exposing the first sensitive functional layer 6, and a distance between the auxiliary layer 7 and the electrode layer 3 may be less than or equal to 100 μm. Taking the auxiliary layer 7 made of a metal material as an example, the auxiliary layer 7 may be prepared by an evaporation process. After forming the auxiliary layer 7, the method of manufacturing the microelectrode structure according to the present disclosure may further include: forming a second sensitive functional layer 8, which covers the auxiliary layer 7 and fills the first through-hole so as to be in contact with the first sensitive functional layer 6. The second sensitive functional layer 8 may be prepared by a spin coating process. In addition, the first through-hole of the auxiliary layer 7 is located outside the opening of the second insulating layer 4. The structure after forming the first sensitive functional layer 6 on the basis of the structure shown in FIG. 12 is shown in FIG. 13.

As shown in FIGS. 14 to 16, FIG. 22 and FIG. 23, the biological detection apparatus according to the embodiments of the present disclosure may include a flexible substrate 12 and a biosensor 13.

The biosensor 13 is provided on the flexible substrate 12 and configured to obtain substance information of a living body.

During use of the biological detection apparatus according to the embodiments of the present disclosure, the flexible substrate 12 is attached to the skin surface of the living body to be detected, and the biosensor 13 is directed toward the living body to be detected, such that the substance information of the living body may be detected through the biosensor 13.

Hereinafter, components of the biological detection apparatus according to the embodiments of the present disclosure will be described in detail.

Figure 14:
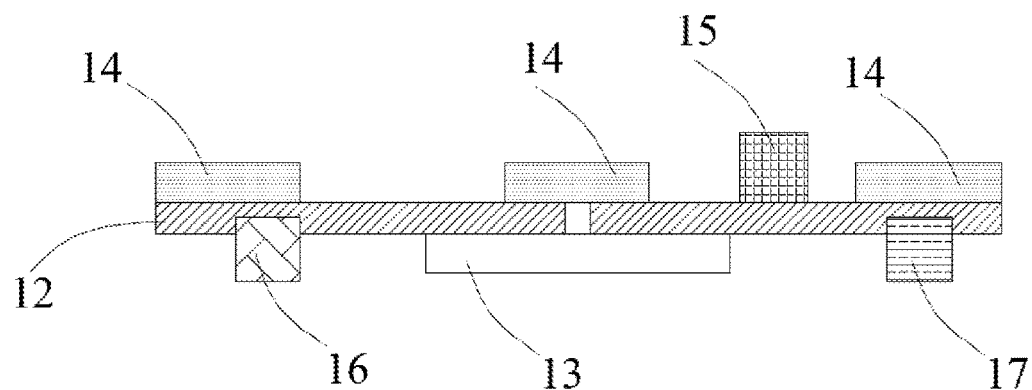
FIG. 14 is a schematic diagram of a biological detection apparatus according to an embodiment of the present disclosure.
Figure 17:
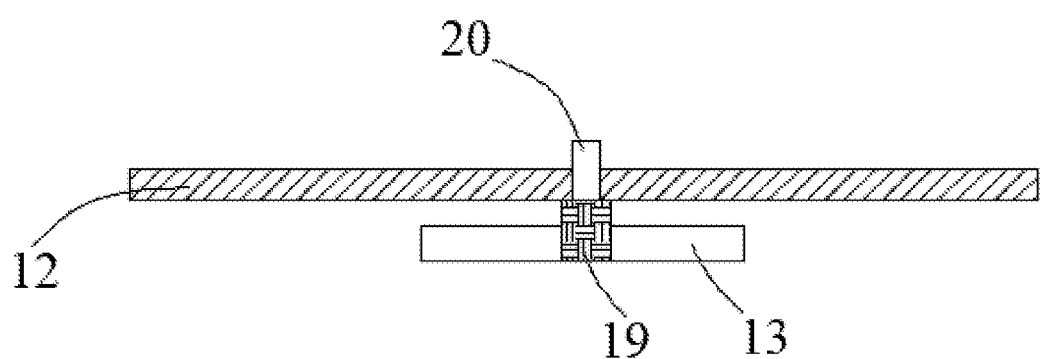
FIG. 17 is a schematic diagram of a flexible substrate and a biosensor in the biological detection apparatus shown in FIG. 14.
Figure 18:
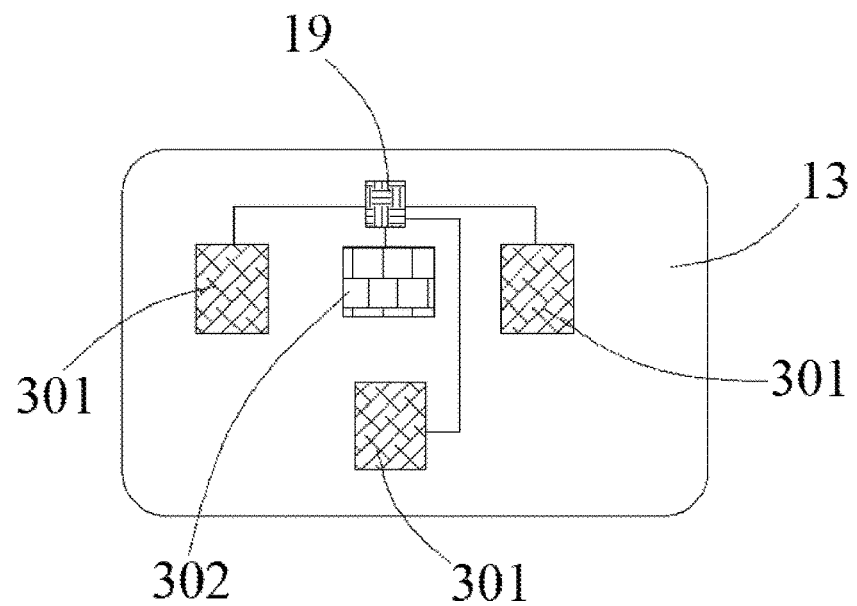
FIG. 18 is a schematic diagram of a biosensor in a biological detection apparatus according to an embodiment of the present disclosure.
Figure 19:
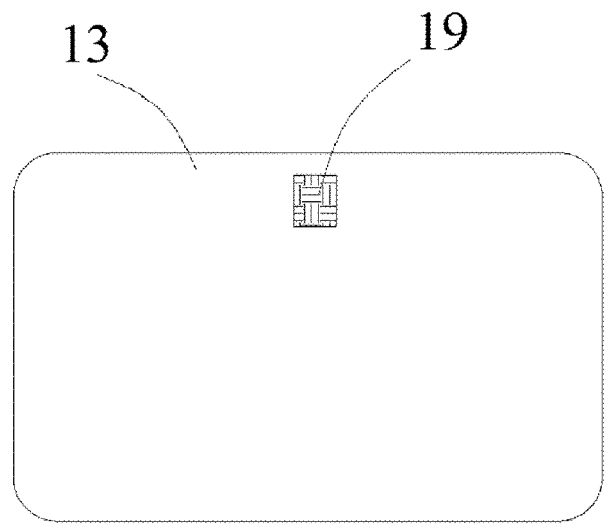
FIG. 19 is a schematic diagram of the other side of the biosensor shown in FIG. 18.
Figure 20:
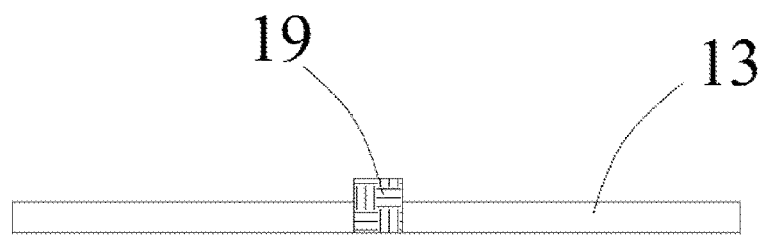
FIG. 20 is a schematic cross-sectional view of a biosensor in a biological detection apparatus according to an embodiment of the present disclosure.
Figure 21:
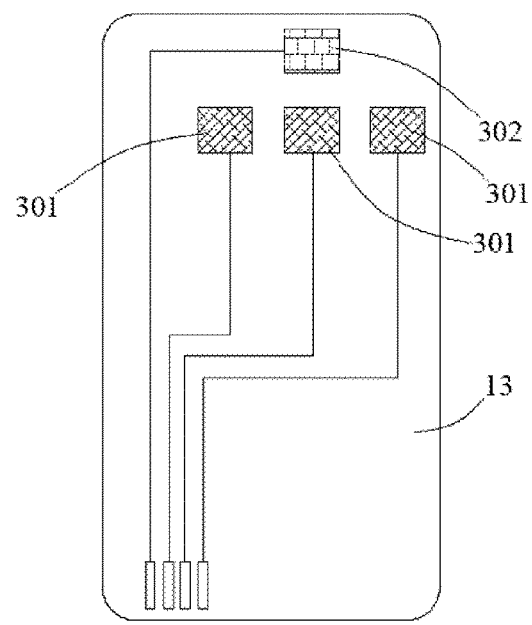
FIG. 21 is another schematic diagram of a biosensor in a biological detection apparatus according to an embodiment of the present disclosure.

As shown in FIG. 14, the flexible substrate 12 serves as a supporting structure for the biological detection apparatus. The flexible substrate 12 may be attached to the skin of the living body. The flexible substrate 12 may be made of a polymer material with good elasticity and good ductility, such that the flexible substrate 12 may be deformed and stretched along with the skin of the living body. For example, the flexible substrate 12 may be made of polyethylene terephthalate (PET), polyimide (PI), polydimethylsiloxane (PDMS), or the like. The flexible substrate 12 may include a first surface and a second surface opposite to each other. When the flexible substrate 12 is attached to the skin of the living body, the first surface of the flexible substrate 12 faces the skin of the living body. In addition, as shown in FIG. 17, a second conductive connection member 20 may be provided on the flexible substrate 12.

Figure 15:
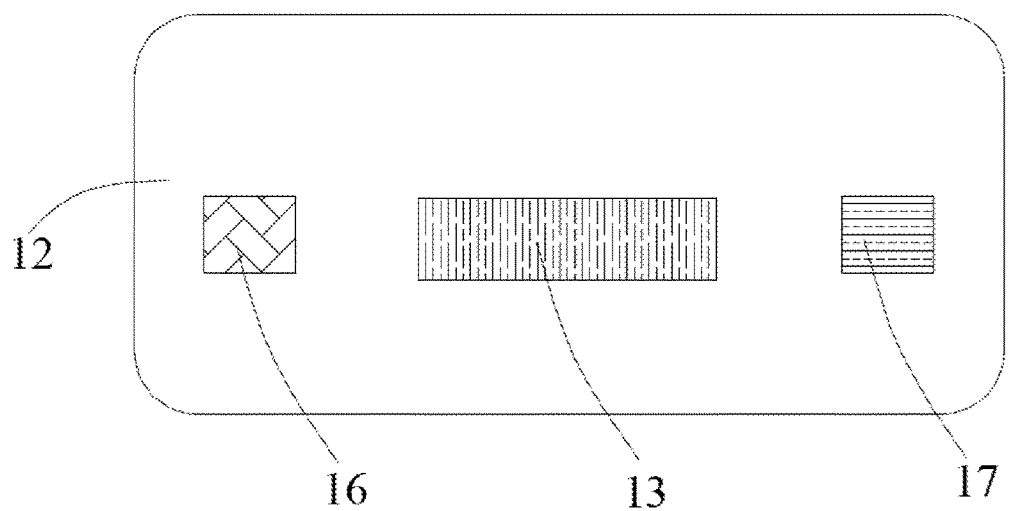
FIG. 15 is a bottom view of the biological detection apparatus shown in FIG. 14.
Figure 22:
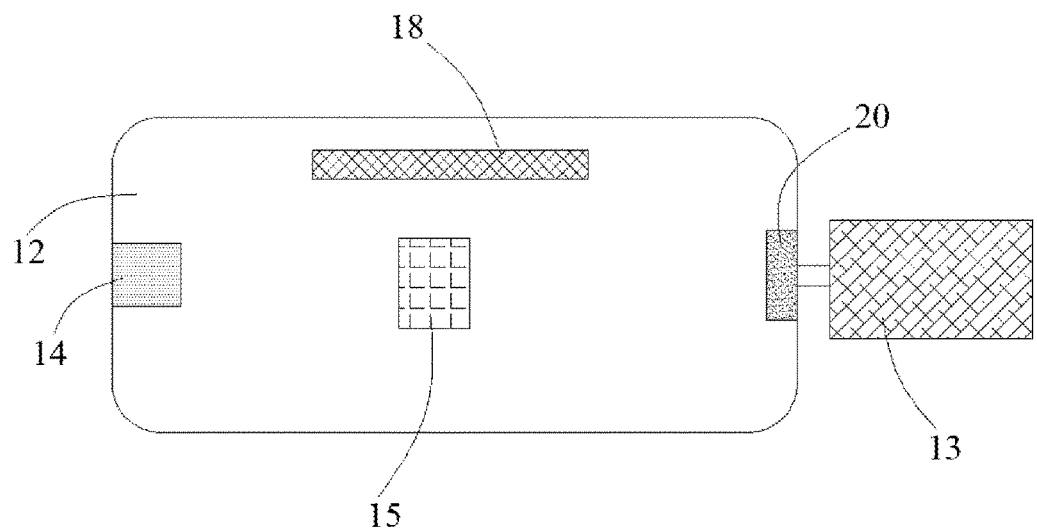
FIG. 22 is a schematic diagram of a biological detection apparatus according to another embodiment of the present disclosure.
Figure 23:
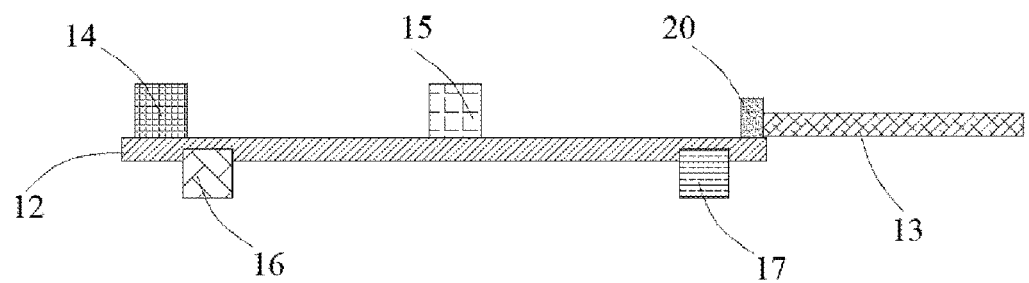
FIG. 23 is a schematic cross-sectional view of the biological detection apparatus shown in FIG. 22.

As shown in FIGS. 14 and 15, and FIGS. 17-21, the biosensor 13 is provided on the flexible substrate 12 and configured to obtain the substance information of the living body. As shown in FIGS. 14 and 15, the biosensor 13 may be provided at a side of the flexible substrate 12 facing the living body, and located within a boundary of the flexible substrate 12. The biosensor 13 is located within the boundary of the flexible substrate 12, which means that, in the case where the flexible substrate 12 is spread out flat, the biosensor 13 is located within the boundary of the flexible substrate 12 in a direction parallel to the flexible substrate 12. The biosensor 13 may be provided on the first surface of the flexible substrate 12 so as to be in contact with the living body, such that the biosensor 13 may detect the substance information of the living body. The substance information may include ion information, glucose information, lactic acid information, and the like. The ion information may include sodium ion information, potassium ion information, chloride ion information, calcium ion information, hydrogen ion information, and the like. The ion information may include information on ions in the sweat of the living body. In another embodiment of the present disclosure, as shown in FIGS. 22 and 23, at least a part of the biosensor 13 is located outside the boundary of the flexible substrate 12, such that the entire biological detection apparatus may be thinner and have a better conformability when in contact with the living body, thereby improving the detection accuracy. The biosensor 13 may be provided with the working electrode regions 301 and the reference electrode region 302 described above. The biosensor 13 may be connected with the second conductive connection member 20 on the flexible substrate 12 through a first conductive connection member 19. The first conductive connection member 19 may be detachably connected with the second conductive connection member 20, for example, in a plug-in connection manner. Since the first conductive connection member 19 may be detachably connected with the second conductive connection member 20, the biosensor 13 on the flexible substrate 12 may be replaced, and the replaced biosensor 13 may be configured to obtain different substance information. However, the replaced biosensor 13 may be configured to obtain the same substance information.

As shown in FIGS. 14 and 15, the biological detection apparatus according to the embodiments of the present disclosure may further include a temperature sensor 16. Taking the biosensor 13 being provided on the first surface of the flexible substrate 12 as an example, the temperature sensor 16 may be provided at the side of the flexible substrate 12 facing the living body, that is, the temperature sensor 16 may also be provided on the first surface of the flexible substrate 12. The temperature sensor 16 is configured to detect temperature information of the living body.

As shown in FIGS. 14 and 15, the biological detection apparatus according to the embodiments of the present disclosure may further include a heart rate sensor 17. Taking the biosensor 13 being provided on the first surface of the flexible substrate 12 as an example, the heart rate sensor 17 may be provided at the side of the flexible substrate 12 facing the living body, that is, the heart rate sensor 17 may also be provided on the first surface of the flexible substrate 12. The heart rate sensor 17 is configured to detect heart rate information of the living body.

Figure 16:
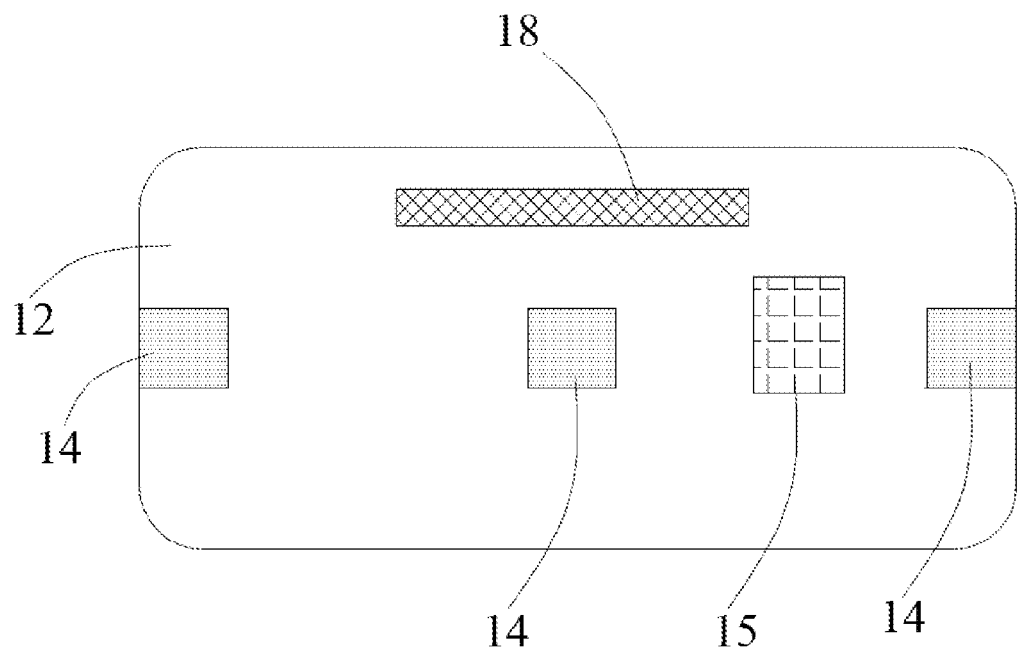
FIG. 16 is a top view of the biological detection apparatus shown in FIG. 14.

As shown in FIGS. 14 to 16, the biological detection apparatus according to the embodiments of the present disclosure may further include a communication module 18. The communication module 18 may be provided on the second surface of the flexible substrate 12. The communication module 18 may include a Bluetooth antenna and the like. The communication module 18 may be connected with the biosensor 13 to send the substance information to a terminal device. The communication module 18 may also be connected with both the temperature sensor 16 and the heart rate sensor 17 to send the temperature information and the heart rate information to the terminal device. The terminal device may be a mobile phone or a computer, etc.

As shown in FIGS. 14 to 16, the biological detection apparatus according to the embodiments of the present disclosure may further include an analog-to-digital converter 15. The analog-to-digital converter 15 may be provided on the second surface of the flexible substrate 12. The analog-to-digital converter 15 may be connected with both the biosensor 13 and the communication module 18, and configured to perform an analog-to-digital conversion on the substance information detected by the biosensor 13 and send the converted substance information to the communication module 18. The analog-to-digital converter 15 may also be connected with both the temperature sensor 16 and the heart rate sensor 17, and configured to perform an analog-to-digital conversion on the temperature information and the heart rate information and send the converted temperature information and heart rate information to the communication module 18. Where, the information before the analog-to-digital conversion is in the form of an analog signal, and the information after the analog-to-digital conversion is in the form of a digital signal.

As shown in FIGS. 14 to 16, the biological detection apparatus according to the embodiments of the present disclosure may further include a power supply module 14. The power supply module 14 is provided at the side of the flexible substrate 12 facing away from the living body, that is, the power supply module 14 is provided on the second surface of the flexible substrate 12. Taking the biosensor 13 being provided on the first surface of the flexible substrate 12 as an example, since the biosensor 13 and the power supply module 14 are located at opposite sides of the flexible substrate 12, rather than at the same side of the flexible substrate 12, the biosensor 13 and the power supply module 14 may be provided on the flexible substrate 12 having a relatively small area at the same time. In other embodiments of the present disclosure, the power supply module 14 may also be provided on the first surface of the flexible substrate 12. The power supply module 14 may be connected with the biosensor 13 to supply power to the biosensor 13. The power supply module 14 may be connected with the above-mentioned second conductive connection member 20, so as to be connected with the biosensor 13. The power supply module 14 may also be connected with the temperature sensor 16, the heart rate sensor 17, the communication module 18 and the analog-to-digital converter 15 to supply power to the temperature sensor 16, the heart rate sensor 17, the communication module 18 and the analog-to-digital converter 15. The power supply module 14 may have a sheet-like structure, for example, the power supply module 14 may be a thin film battery. A joint surface between the sheet-like power supply module 14 and the flexible substrate 12 may have an increased area, such that the biosensor 13 may be stably disposed on the flexible substrate 12 through the power supply module 14, so as to prevent the biosensor 13 from wrinkling.

The above biosensor 13 may include the microelectrode structure according to the above embodiments. As shown in FIG. 14, the first insulating layer of the microelectrode structure may be provided on the first surface of the flexible substrate 12. The electrode layer of the microelectrode structure may be provided at a side of the first insulating layer facing away from the flexible substrate 12. During use, the microelectrode structure is in contact with the living body. As shown in FIG. 17, since the first conductive connection member 19 is detachably connected with the second conductive connection member 20, the biosensor 13 on the flexible substrate 12 may be replaced. Taking the microelectrode structure including the protrusion as an example, the protrusions of the microelectrode structures in the biosensors 13 before and after replacement may have different heights, so as to measure different substance information.

The embodiments of the present disclosure may also provide a biological detection system. The biological detection system may include the biological detection apparatus according to any of the above embodiments. The biological detection system may further include a terminal device. The terminal device may be communicatively connected with the biosensor to process or display the substance information detected by the biosensor. The terminal device may be a mobile phone, a computer, etc. The biological detection apparatus included in the biological detection system according to the embodiment of the present disclosure and the biological detection apparatus according to the above embodiments are the same, and thus have the same beneficial effects, which will not be repeated herein.

The embodiments of the present disclosure may also provide a biological detection method. The biological detection method may use the biological detection apparatus according to any of the above embodiments. The biological detection method may include: obtaining first substance information of a living body by using a biological detection apparatus; and replacing a biosensor of the biological detection apparatus to obtain second substance information of the living body. The first substance information and the second substance information may have the same meaning as the substance information in the embodiments of the above biological detection apparatus. For example, the first substance information or the second substance information may include a sodium ion concentration, a potassium ion concentration, a calcium ion concentration, a hydrogen ion concentration, or a chloride ion concentration.

The above are merely some embodiments of the present disclosure, and not intended to limit the present application in any form. Although the present disclosure has been disclosed as above in some embodiments, the present disclosure is not limited thereto. Any person skilled in the art may utilize the technical contents disclosed above to make some variations or modifications into equivalent embodiments with equivalent changes, without departing from the scope of the present disclosure. However, without departing from the contents of the present disclosure, any simple variations, equivalent changes and modifications made to the above embodiments based on the technical essence of the present disclosure still fall within the scope of the present disclosure.

The invention claimed is:
1. A biological detection apparatus, comprising:
a flexible substrate; and
a biosensor provided on the flexible substrate and configured to obtain substance information of a living body,
wherein the biosensor comprises a microelectrode structure, the microelectrode structure comprising:
a first insulating layer;
a protrusion provided at a side of the first insulating layer;
an electrode layer conformally covering the first insulating layer and the protrusion;
a second insulating layer provided at a side of the electrode layer facing away from the first insulating layer, and provided with an opening through which the protrusion protrudes;

a first sensitive functional layer at least covering an area of the electrode layer corresponding to an entirety of the protrusion;
an auxiliary layer at least covering an area of the first sensitive functional layer corresponding to an entirety of the protrusion except for a first through-hole exposing only part of the first sensitive functional layer, wherein the first through-hole is provided in an area of the auxiliary layer corresponding to a top end of the protrusion; and
a second sensitive functional layer entirely covering the auxiliary layer and filling the first through-hole so as to be in contact with the first sensitive functional layer,
wherein the electrode layer is sandwiched between the first and second insulating layers corresponding to an area where there are no protrusions, and the auxiliary layer is sandwiched between the first sensitive functional layer and the second sensitive functional layer.

2. The biological detection apparatus according to claim 1, further comprising:
a communication module, provided at a side of the flexible substrate and connected with the biosensor, and configured to send the substance information to a terminal device; and
an analog-to-digital converter, provided at the side of the flexible substrate and connected with the biosensor and the communication module, and configured to perform an analog-to-digital conversion on the substance information and send the converted substance information to the communication module.

3. The biological detection apparatus according to claim 1, wherein the biosensor is provided at a side of the flexible substrate facing the living body and located within a boundary of the flexible substrate.

4. The biological detection apparatus according to claim 1, wherein at least a part of the biosensor is located outside a boundary of the flexible substrate.

5. The biological detection apparatus according to claim 1, further comprising at least one of:
a temperature sensor, provided at a side of the flexible substrate facing the living body and configured to detect temperature information of the living body; or
a heart rate sensor, provided at the side of the flexible substrate facing the living body and configured to detect heart rate information of the living body.

6. The biological detection apparatus according to claim 1, further comprising:
a power supply module, provided at a side of the flexible substrate facing away from the living body and connected with the biosensor to supply power to the biosensor.

7. The biological detection apparatus according to claim 1, wherein an angle between a side surface and a bottom surface of the protrusion is an acute angle.

8. The biological detection apparatus according to claim 7, wherein the protrusion has a tapered shape.

9. The biological detection apparatus according to claim 1,
wherein the protrusion has a maximum width of less than or equal to 10 μm in a direction parallel to the first insulating layer, and
the protrusion is made of an insulating material.

10. The biological detection apparatus according to claim 1, wherein the protrusion and the first insulating layer are structurally integrated.

11. The biological detection apparatus according to claim 1, wherein the electrode layer comprises one or more electrode regions separated from each other, and the first insulating layer is provided with a plurality of protrusions correspondingly to each of the electrode regions.

12. The biological detection apparatus according to claim 1, wherein the electrode layer comprises a reference electrode region and one or more working electrode regions; or
the electrode layer comprises a reference electrode region, a counter electrode region and one or more working electrode regions.

13. The biological detection apparatus according to claim 1, wherein the electrode layer comprises one or more electrode regions separated from each other, and a distance between adjacent two of the electrode regions is 0.5 cm-2 cm.

14. The biological detection apparatus according to claim 1, wherein a distance between the auxiliary layer and the electrode layer is less than or equal to 100 μm.

15. The biological detection apparatus according to claim 1, wherein the first sensitive functional layer comprises a sodium ion sensitive functional layer, a potassium ion sensitive functional layer, a calcium ion sensitive functional layer, a hydrogen ion sensitive functional layer or a chloride ion sensitive functional layer.

16. The biological detection apparatus according to claim 1, wherein the biosensor is configured to detect the substance information in sweat of the living body.

17. A biological detection system, comprising a biological detection apparatus, wherein the biological detection apparatus comprises:
a flexible substrate; and
a biosensor provided on the flexible substrate and configured to obtain substance information of a living body,
wherein the biosensor comprises a microelectrode structure, the microelectrode structure comprising:
a first insulating layer;
a protrusion provided at a side of the first insulating layer;
an electrode layer conformally covering the first insulating layer and the protrusion; and
a second insulating layer provided at a side of the electrode layer facing away from the first insulating layer, and provided with an opening through which the protrusion protrudes;
a first sensitive functional layer at least covering an area of the electrode layer corresponding to an entirety of the protrusion;
an auxiliary layer at least covering an area of the first sensitive functional layer corresponding to an entirety of the protrusion except for a first through-hole exposing only part of the first sensitive functional layer, wherein the first through-hole is provided in an area of the auxiliary layer corresponding to a top end of the protrusion;
a second sensitive functional layer entirely covering the auxiliary layer and filling the first through-hole so as to be in contact with the first sensitive functional layer,
wherein the electrode layer is sandwiched between the first and second insulating layers corresponding to an area where there are no protrusions, and the auxiliary layer is sandwiched between the first sensitive functional layer and the second sensitive functional layer.

18. A biological detection method, comprising:
obtaining first substance information of the living body by using the biosensor of the biological detection apparatus according to claim 1; and replacing the biosensor of the biological detection apparatus to obtain second substance information of the living body.

19. The biological detection method according to claim 18, wherein the first substance information or the second substance information comprises a sodium ion concentration, a potassium ion concentration, a calcium ion concentration, a hydrogen ion concentration, or a chloride ion concentration.

* * * * *